(12) United States Patent
Jawidzik

(10) Patent No.: US 10,901,450 B2
(45) Date of Patent: Jan. 26, 2021

(54) MULTI-FUNCTIONAL SURGICAL FOOT CONTROLLER WITH INTEGRATED SHROUD

(71) Applicant: Alcon Inc., Fribourg (CH)

(72) Inventor: Geoffrey C. Jawidzik, Mission Viejo, CA (US)

(73) Assignee: Alcon Inc., Fribourg (CH)

(*) Notice: Subject to any disclaimer, the term of this patent is extended or adjusted under 35 U.S.C. 154(b) by 0 days.

(21) Appl. No.: 16/545,219

(22) Filed: Aug. 20, 2019

(65) Prior Publication Data

US 2020/0064879 A1 Feb. 27, 2020

Related U.S. Application Data

(60) Provisional application No. 62/720,179, filed on Aug. 21, 2018.

(51) Int. Cl.
| | | |
|---|---|---|
| G05G 1/38 | (2008.04) | |
| G05G 5/05 | (2006.01) | |
| G05G 1/44 | (2008.04) | |
| A61F 9/007 | (2006.01) | |
| A61F 9/008 | (2006.01) | |
| G05G 1/01 | (2008.04) | |

(52) U.S. Cl.
CPC .......... *G05G 1/38* (2013.01); *A61F 9/00745* (2013.01); *A61F 9/00821* (2013.01); *G05G 1/01* (2013.01); *G05G 1/44* (2013.01); *G05G 5/05* (2013.01); *A61F 2009/00874* (2013.01); *G05G 2505/00* (2013.01)

(58) Field of Classification Search
CPC .. G05G 1/38; G05G 1/01; G05G 1/44; G05G 5/05; A61F 9/00745
USPC ........................................................ 200/86.5
See application file for complete search history.

(56) References Cited

U.S. PATENT DOCUMENTS

| | | |
|---|---|---|
| 6,179,829 B1 | 1/2001 | Bisch |
| 6,659,998 B2 | 12/2003 | Dehoogh et al. |
| 6,689,975 B2 | 2/2004 | Hall |
| 6,862,951 B2 | 3/2005 | Peterson |
| 6,962,581 B2 | 11/2005 | Thoe |
| 7,012,203 B2 | 3/2006 | Hanson |
| 7,019,234 B1 | 3/2006 | Mezhinsky |
| 7,084,364 B2 | 8/2006 | Mezhinsky |
| 7,470,277 B2 | 12/2008 | Finlay |
| 7,619,171 B2 | 11/2009 | Horvath |
| 7,626,132 B2 | 12/2009 | Mezhinsky |
| 8,465,473 B2 | 6/2013 | Horvath |
| 8,680,412 B2 | 3/2014 | Horvath |
| 8,749,188 B2 | 6/2014 | Tran |
| 9,240,110 B2 | 1/2016 | Roth |
| 9,439,806 B2 | 9/2016 | Eastman |
| 9,795,507 B2 | 10/2017 | Hajishah |
| 10,243,557 B2 | 3/2019 | Ekvall |
| 2003/0132092 A1 | 7/2003 | Hall |

(Continued)

FOREIGN PATENT DOCUMENTS

| | | |
|---|---|---|
| EP | 1714617 A1 | 10/2006 |
| JP | 4522483 B1 | 6/2010 |

*Primary Examiner* — Nguyen Tran
*Assistant Examiner* — Iman Malakooti

(57) ABSTRACT

Multi-functional foot controller with treadle for controlling a first function and as an integrated shroud for a switch that controls an additional function.

20 Claims, 7 Drawing Sheets

(56) References Cited

U.S. PATENT DOCUMENTS

| | | | |
|---|---|---|---|
| 2004/0106915 A1* | 6/2004 | Thoe | A61B 17/00 |
| | | | 606/1 |
| 2006/0219049 A1* | 10/2006 | Horvath | H01H 21/26 |
| | | | 74/560 |
| 2007/0043339 A1 | 2/2007 | Horvath | |
| 2008/0114387 A1 | 5/2008 | Hertweck | |
| 2008/0243105 A1* | 10/2008 | Horvath | A61B 17/32002 |
| | | | 606/1 |
| 2010/0198200 A1 | 8/2010 | Horvath | |
| 2014/0364864 A1 | 12/2014 | Lynn | |
| 2015/0173725 A1 | 6/2015 | Maxson | |
| 2015/0305936 A1 | 10/2015 | Hajishah | |
| 2016/0106581 A1 | 4/2016 | Gonzalez | |
| 2018/0132958 A1 | 5/2018 | Jochinsen | |
| 2019/0350757 A1 | 11/2019 | Charles | |
| 2020/0085515 A1 | 3/2020 | Jawidzik | |

* cited by examiner

MULTI-FUNCTIONAL SURGICAL FOOT CONTROLLER WITH INTEGRATED SHROUD

BACKGROUND

Field of the Disclosure

The present disclosure relates to a foot controller and, more specifically, to a multi-functional surgical foot controller with a laser switch and integrated shroud.

Description of Related Art

Patient treatment apparatus or surgical systems, such as surgical equipment used when performing ophthalmic surgery, may require controlling a variety of subsystems, such as pneumatic and electronically driven subsystems, therapeutic lasers, etc.

The operation of the subsystems can be controlled by a microprocessor-driven console. The microprocessor controls within a surgical console receive mechanical inputs from either the operator of the surgical system or from an assistant to govern the operation of a subsystem within the patient treatment apparatus. Control input devices may include switches on the console, remote hand switches, remote foot controllers, and other control input devices.

Some procedures benefit from a treadle-driven foot controller which, like regulating speed with a pedal of an automobile, allows an operator to regulate a variable control input, e.g. cut speed of a vitrectomy probe. For these treadle-driven foot controllers, the mechanical inputs can originate from the movement of the foot of an operator which are translated into electrical signals that are fed to the microprocessor controls. Other procedures require binary control of an input, such as procedures involving a therapeutic laser. Also, in many surgical procedures it is necessary to switch from one type of surgical instrument to another, for example, from a vitrectomy probe to a therapeutic laser probe. Typically, a different foot controller is provided for each surgical console or instrument. With multiple surgical instruments in use during a procedure, the operation environment can become cluttered with control devices. Also, there exist standards for surgical lasers which require that a foot controller used to control a laser include a shroud to guard against accidental laser activation.

Previous attempts to integrate the functionality of a treadle-driven foot controller with a laser controller include incorporation of a moveable shroud into the heel-region of the base of a foot controller. The movable shroud can be lifted up by the operator using the toe region of their foot, to gain access to a switch for a laser emission control switch. However, procedures that utilize a therapeutic laser (e.g. a vitrectomy and pan-retinal photocoagulation procedure) are extremely delicate procedures where unnecessary movements and removal of tools from the surgical site and subsequent re-introduction of the tools should be avoided to optimize patient outcome. These previous attempts to integrate treadle-driven foot controller with a laser controller require a surgeon to take his or her focus away from the procedure to look down at a footswitch to re-orientate their foot, open the shroud, and gain access to the switch, which may lead to risky hand movement and/or removal of tools from the surgical site.

SUMMARY

The disclosed embodiments of the present technology relate to a multi-functional foot controller with an integrated shroud that allows an operator to intuitively switch between functions.

Some embodiments of the present technology involve a foot controller with a treadle coupled with a base. The treadle has a pair of side supports rotatably coupled with the base with the pair of side supports separated by a gap. The foot controller can include a spring assembly that places the pedal surface of the treadle at the default angular position with respect to the base and configured to compress with the application of torque on the pedal surface by a downward rotational depression of the treadle. The foot controller also includes a control assembly that determines the angular position of the treadle relative to the base and to converts the angular position into a first signal describing the angular position of the pedal surface. In addition, the foot controller is communicatively coupled with a console and the signal can be used to control the console, a console accessory, and/or another module used in conjunction with the console.

In some embodiments, the treadle also has a pedal surface coupled with the pair of side supports at the distal end of the treadle. A gap between the pair of side supports accommodates an object for providing an upward rotational lift on a bottom surface of the pedal surface. The foot controller also includes a switch configured to emit an additional signal upon depression of the switch. The foot controller is communicatively coupled with a therapeutic laser module, and wherein the additional signal is used to control the emission of one or more laser from the therapeutic laser module. For safety reasons, a switch controlling a therapeutic laser should be shrouded and, according to the present technology, the switch is positioned at the distal end of the base and is at least partially shrouded by the pedal surface at a default angular position of the pedal surface relative to the base. To provide multi-functionality to the foot controller, the switch is exposed upon an upward rotational lift of the pedal surface of the pedal surface away from the distal end of the base. In some cases, a raised rotational position of the treadle after the upward rotational lift of the pedal surface is maintained (e.g. by a ball plunger and detent) until the operator removes his foot from beneath the pedal surface and depresses the pedal surface.

In some embodiments, the underside of the pedal surface contains a recess positioned such that the switch is at least partially housed in the recess after a downward rotational depression of the pedal surface toward the distal end of the base. In some cases, the switch and the pedal surface are arranged such that the switch is not actuated upon a maximum downward rotational depression of the pedal surface toward the distal end of the base.

In some embodiments, the base includes a heel rest area in the area of a proximal end of the base and a depression in the substantially flat surface in a position of an arch of an operator's foot when the operator's foot is placed on the base with a heel proximal to the heel rest area and a toe end substantially on the pedal surface. The depression allows the operator to insert a top surface of the operator's foot into the depression and under the pedal surface, provide the upward rotational lift on a bottom surface of the pedal surface, and actuate the switch with the bottom surface of the operator's foot. In some cases, the bottom surface of the pedal surface is rounded for facilitating a smooth entry of the operator's foot and an easy withdrawal of the operator's foot from under the pedal surface.

BRIEF DESCRIPTION OF THE DRAWINGS

For a more complete understanding of the present technology, its features, and its advantages, reference is made to the following description, taken in conjunction with the accompanying drawings, in which.

DESCRIPTION

The technology described below involves a multi-functional foot controller with an integrated shroud that allows an operator to easily switch between functions. The foot controller can include a treadle that is rotationally depressed to control a first tool, which at least partially shrouds a switch for controlling an additional tool, and which can be easily and intuitively lifted to expose the switch.

Figure 1:
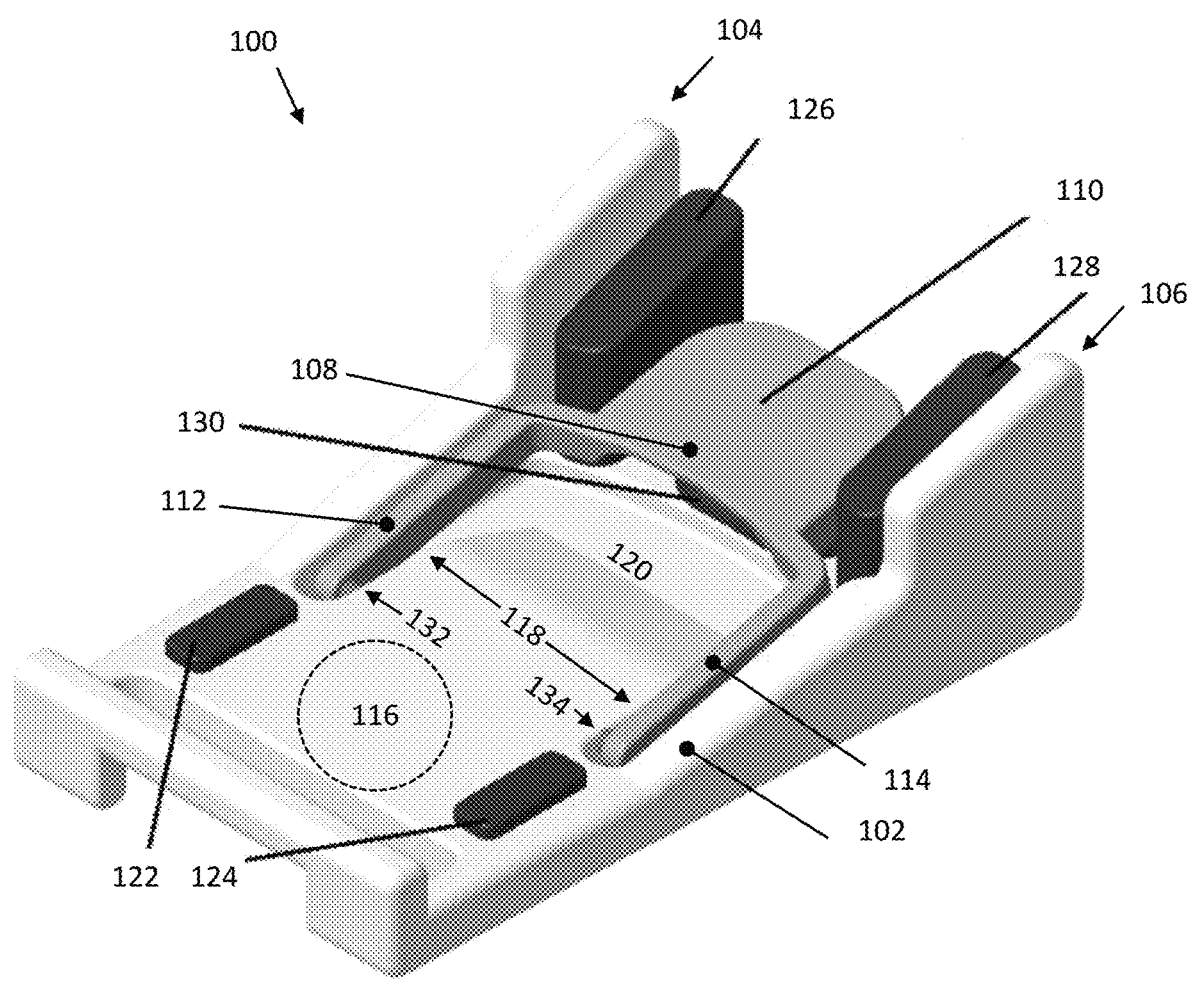
FIG. 1 illustrates a foot controller with an integrated shroud according to some embodiments of the present technology.

FIG. 1 illustrates a foot controller 100 with a substantially flat base 102, a pair of sidewalls 104, 106, and a treadle 108. The treadle 108 includes a pair of side supports 112, 114 rotatably coupled with the base 102 via couplings 132, 134. The treadle 108 also includes a pedal surface 110 at a distal end of the treadle 108. The base 102 of the foot controller includes a heel rest area 116. In addition, the base 102 has a general size and shape that positions the ball/toes of an operator's foot on the pedal surface 110 when the operator's heel is positioned on or near the heel rest area 116.

The rotational coupling of the treadle 108 with the base 102 allows the operator to depress rotationally the pedal surface 110 with a downward articulation of the operator's foot. The foot controller 100 also includes a control assembly (not shown) which determines the angular position of the treadle 108 relative to the base 102 and converts the angular position into a signal. The foot controller 100 can be communicatively coupled with a console and the signal can be used to control the console, a console accessory, and/or another module used in conjunction with the console. For example, the foot controller 100 can be coupled with an ophthalmic surgical console and the signal from the control assembly can be used to control an ophthalmic surgical tool, e.g. a vitrectomy probe, a phacoemulsification hand piece, display settings, etc.

In some cases, the control assembly includes a position sensor (not shown). The position sensor can be rotationally coupled to the treadle 108 through one or both of the couplings 132, 134, either directly or through intermediate mechanical couplings such as gears. If gears are used, it is possible for the rotational motion to be mechanically amplified or attenuated according to the ratio of the number of teeth of the respective gears, as is well known. The position sensor may work through numerous possible well known mechanisms, for example, use of an optical encoder, or use of a potentiometer.

As further illustrated in FIG. 1, the pair of side supports 112, 114 are separated by a gap 118 arranged such that an operator can move his foot within the gap 118 and interface the bottom surface of the pedal surface 110 with the top of the operator's foot. The base 102 can also include a depression 120, which allows the operator's foot to more easily move under the pedal surface 110. In some embodiments, the bottom surface of the pedal surface 110 is rounded to allow smooth ingress and egress.

The rotational coupling of the treadle 108 with the base 102 also allows the operator to rotationally lift the pedal surface 110, after moving the operator's foot under the pedal surface 110, with an upward articulation of the operator's foot on the bottom surface of pedal surface 110.

The foot controller 100 also includes a switch 130 located at or near a distal end of the base 102 substantially beneath the pedal surface 110. When pressed, the switch 130 emits an additional signal for controlling the console, a console accessory, and/or another module used in conjunction with the console. For example, the foot controller 100 can be coupled with an ophthalmic surgical console with an integrated laser module or an ophthalmic surgical console used in conjunction with a stand-alone laser module and the signal from the switch 130 can be used to control one or more laser function of the laser module.

The pedal surface 110 of the treadle 108 acts as a shroud for the switch 130. In other words, the arrangement of the treadle 108 on the base 102 and the arrangement of the switch 130 avoids the switch 130 being actuated by the pedal surface 110 upon a downward rotational depression of the treadle 108—even after a maximum downward rotational depression of the treadle 108. In some cases, the foot controller 100 is arranged such that the maximum downward rotational depression of the treadle 108 positions the treadle approximately between 0° and 5° with respect to the base 102.

Additionally, the switch 130 can be at least partially exposed upon an upward rotational lift of the pedal surface 110 of the treadle 108. In addition, the switch 108 is at least partially shrouded or completely shrouded by the pedal surface 110 at a default angular position of the pedal surface 110 and the range of depressed angular positions of the pedal surface 110. In some embodiments, the bottom surface of the pedal surface 110 has a recess that accommodates a top portion of the switch 130 after a downward rotational depression of the treadle 108, as shown in greater detail below.

The foot controller 100 can also include one or more mechanism (not shown) for maintaining the raised rotational position of the treadle 108 after the upward rotational lift of the pedal surface 110 and for keeping the switch 130 at least partially exposed. For example, the couplings 132, 134 can be rotational joints and can include a ball plunger that engages a feature in the base at a particular raised rotational position of the treadle 108.

In some cases, the treadle 108 includes a single side support arranged substantially adjacent to one of the side walls 104, 106 that is coupled to the pedal surface 110 such that the treadle has a general L-shape. In this configuration, an operator can press the pedal surface downward to achieve rotational depression of the treadle 108. Also, in this arrangement, a hollow corner replaces the gap 118 of the two-support arrangement and an operator can move his foot within hollow corner and interface the bottom surface of the pedal surface 110 the top of the operator's foot to rotationally lift the pedal surface 110.

In some cases, the foot controller 100 also includes a spring assembly (not shown) coupled to the base 102 and to the treadle 108. The spring assembly can be arranged to place the pedal surface 110 of the treadle 108 at a default angular position with respect to the base 102. For example, the default angular position can be selected in a range of approximately 9°-14° with respect to the base 102. As mentioned above, the default angular position of the pedal surface 110 at least partially shrouds or completely shrouds the switch 130. In addition, the spring assembly can compress with the application of torque on the pedal surface 110 by a downward rotational depression of the treadle 108.

As shown in FIG. 1, the foot controller 100 also includes heel buttons 122, 124 at the proximal end of the base 102 and toe buttons 126, 128 at the distal end of the base 102. The heel buttons 122, 124 and the toe buttons 126, 128 can be used to generate signals for controlling a wide variety of functions of a console, console module, and/or a standalone module communicatively coupled with the foot controller 100 and/or the console. For example, due to safety concerns regarding the use of a therapeutic laser on human anatomy, a laser lockout override signal can be required before the use of the therapeutic laser and one or more of the heel buttons 122, 124 can be used to generate the override signal. A wide variety of alternative controls can also be used to override a lockout mechanism including one or more button press, a voice gesture recognized by the console, etc.

Figure 2:
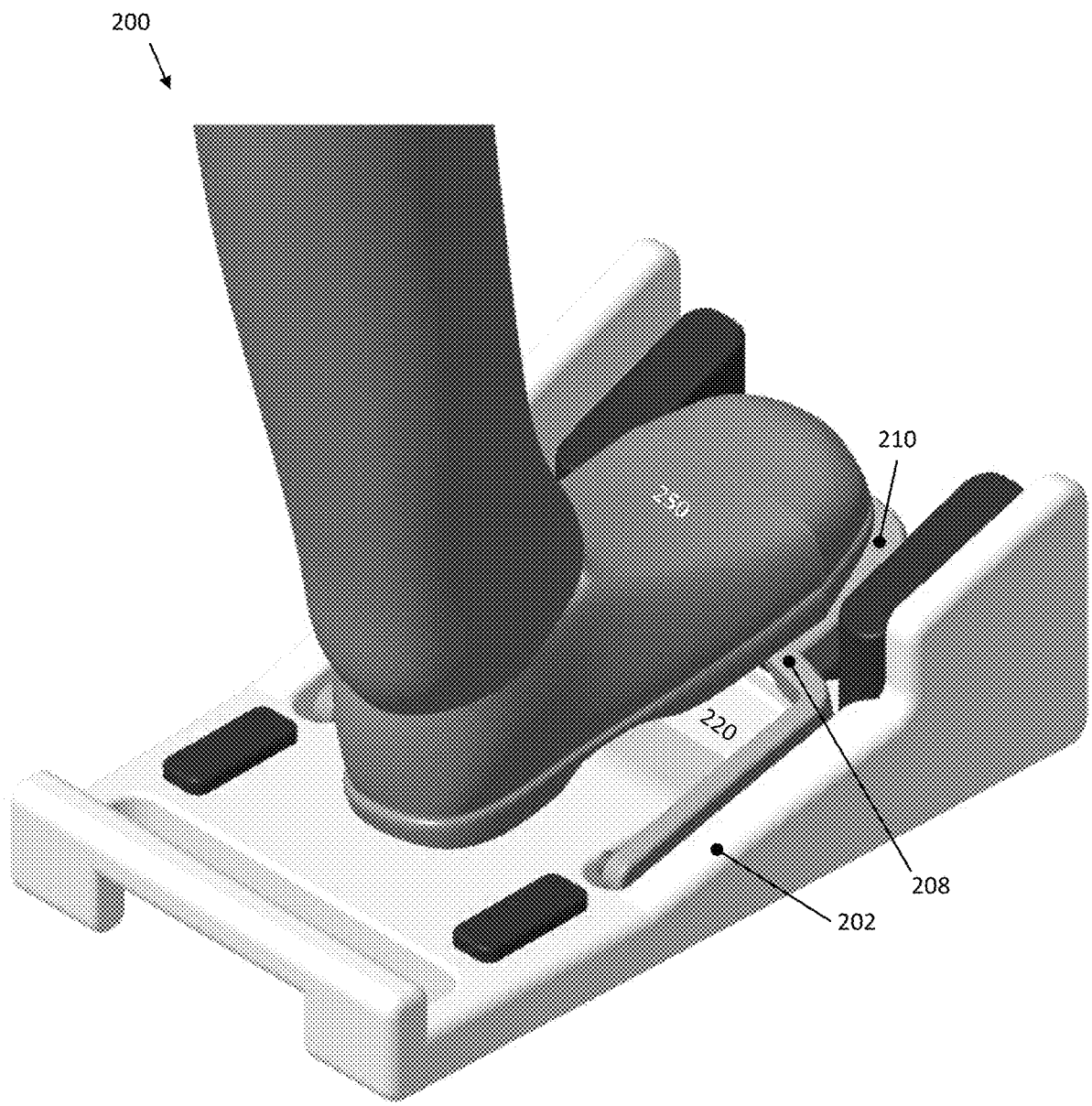
FIG. 2 illustrates a foot controller with an operator's foot placed on a treadle that shrouds a switch.

FIGS. 2-6 illustrate a foot controller 200 according to some embodiments of the present technology. In FIG. 2, an operator's foot 250 is placed on the base 202 of the foot controller 200 with the heel of the operator's foot 250 in a heel rest area (not labeled), the arch of the operator's foot 250 substantially over a depression 220 in the base 202, and the toes of the operator's foot 250 on the pedal surface 210 of a treadle 208.

In this arrangement, the operator can rotationally depress the pedal surface 210 with a downward articulation of the operator's foot 250. The foot controller 200 also includes a control assembly (not shown) which determines the angular position of the treadle 208 relative to the base 202 and converts the angular position into a signal, e.g. for controlling an ophthalmic surgical tool coupled with a console communicatively coupled with the foot controller 200. As shown in FIG. 2, the switch (not labeled) located on the base 202 underneath the pedal surface 210 is at least partially shrouded by the pedal surface 210.

Figure 3A:
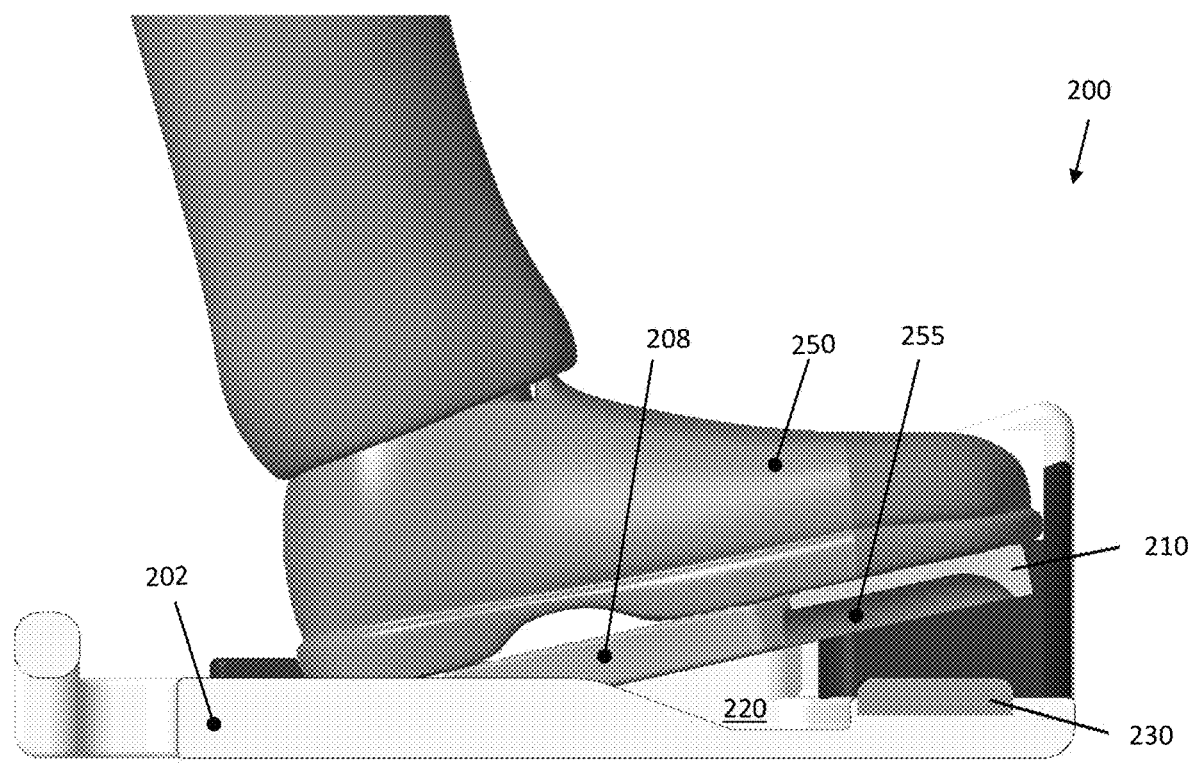
FIG. 3A illustrates a side, cutaway view of a foot controller with a treadle angular position with respect to the base.
Figure 3B:
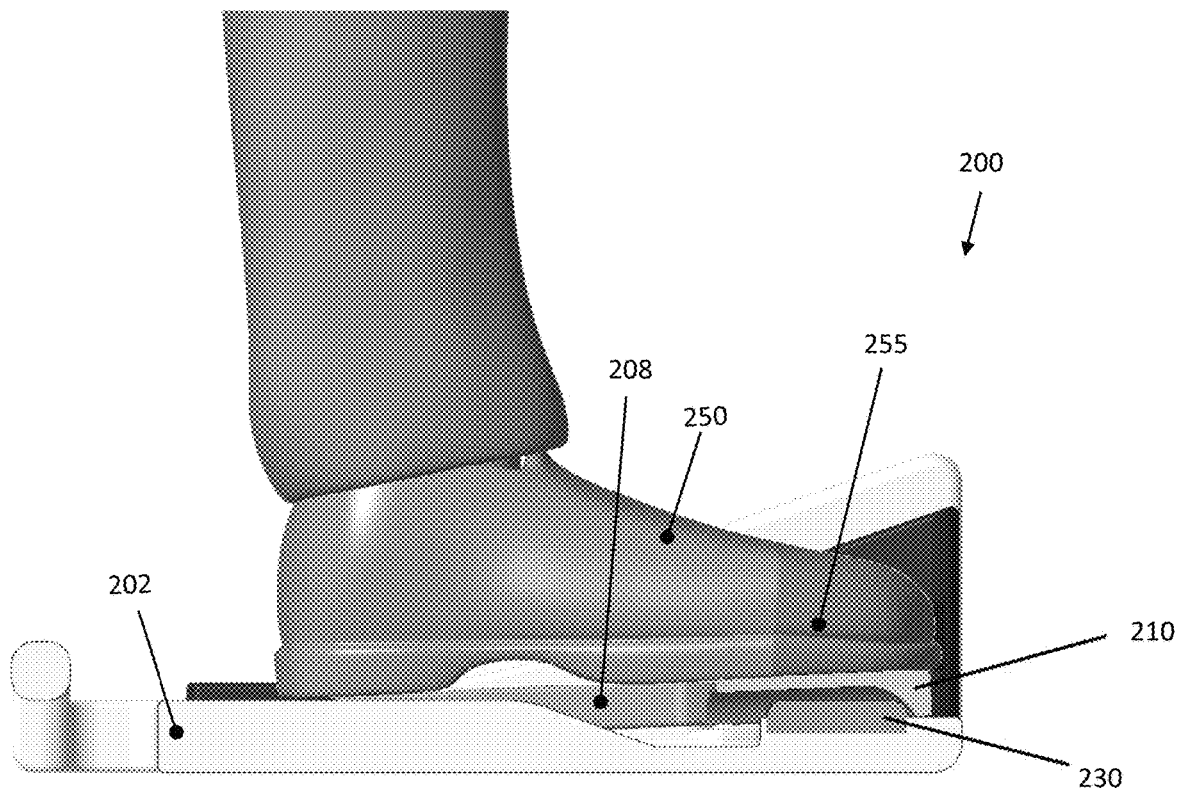
FIG. 3B illustrates a side, cutaway view of a foot controller with the treadle in a fully depressed position after a maximum downward rotational depression of the pedal surface.

FIGS. 3A-3B illustrate side, cutaway views of the foot controller 200. In FIG. 3A, the treadle 208 is in a default angular position with respect to the base 202 before the application of a rotational depression of the pedal surface 210 by the operator's foot 250. In some cases, the default angular position of the treadle 208 can be maintained by a spring assembly (not shown), which also provides resistance to rotational depression of the treadle 208.

Also shown in FIG. 3A, the switch 230 located on the base 202 underneath the pedal surface 210 is at least partially shrouded by the pedal surface 210 when the treadle 208 is in a default angular position. In addition, the bottom surface of the pedal surface 210 contains a recess 255.

FIG. 3B illustrates the treadle 208 in a fully depressed position after a maximum downward rotational depression of the pedal surface 210 by the operator's foot 250. As shown, the switch 230 is not articulated even after the maximum downward rotational depression of the pedal surface 210 due to the arrangement of the switch 230 on the base 202 of the foot controller 200 and the recess 255.

Figure 4:
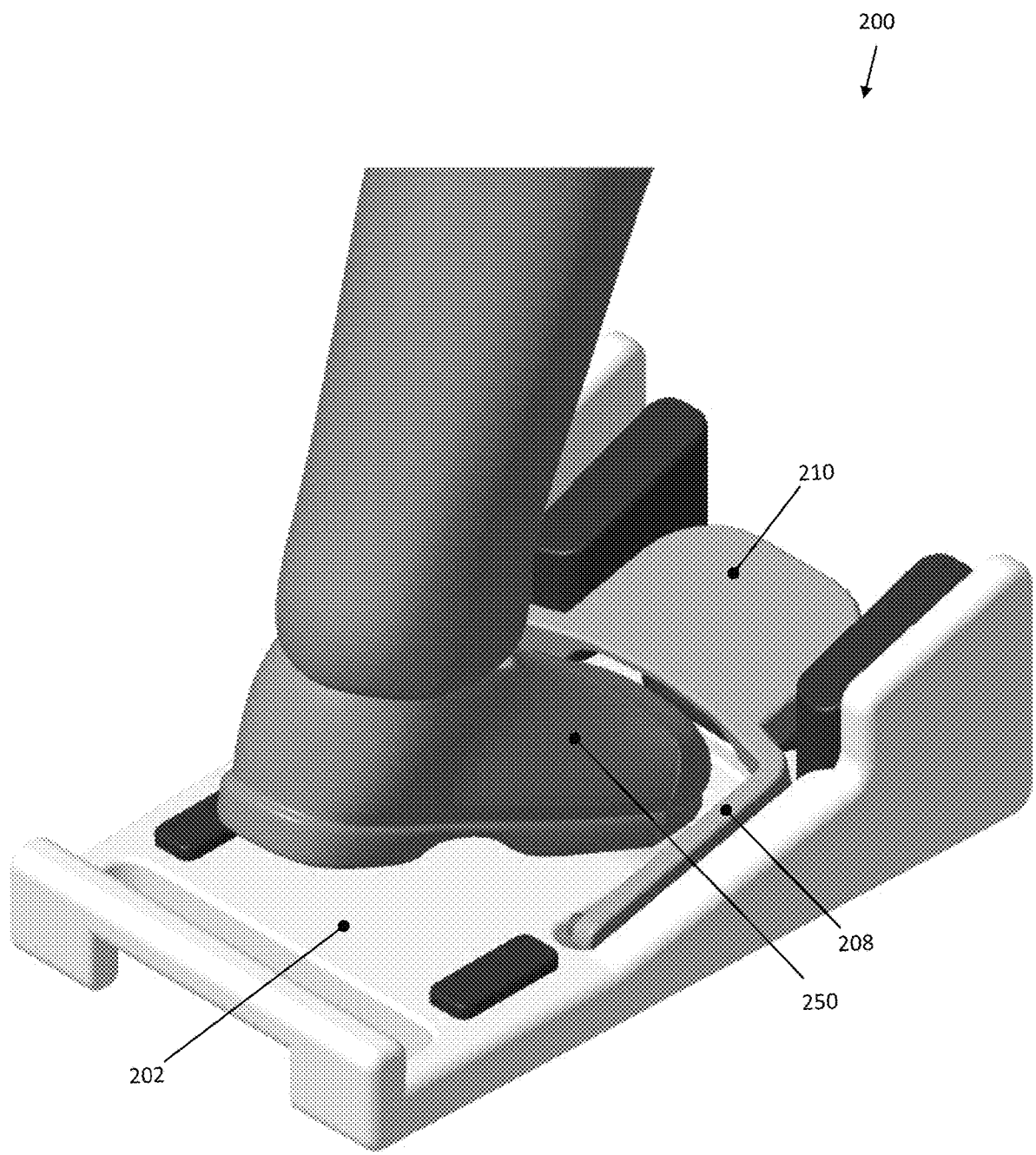
FIG. 4 illustrates a foot controller with an operator's foot in a gap between the side supports of a treadle.

FIG. 4 illustrates the foot controller 200 with the operator's foot 250 moved into the gap (not labeled) between the side supports (not labeled) of a treadle 208. The toes of the operator's foot 250 have been placed into the depression (not labeled) of the base 202 and underneath the bottom surface of the pedal surface 210 of the treadle 208.

Figure 5A:
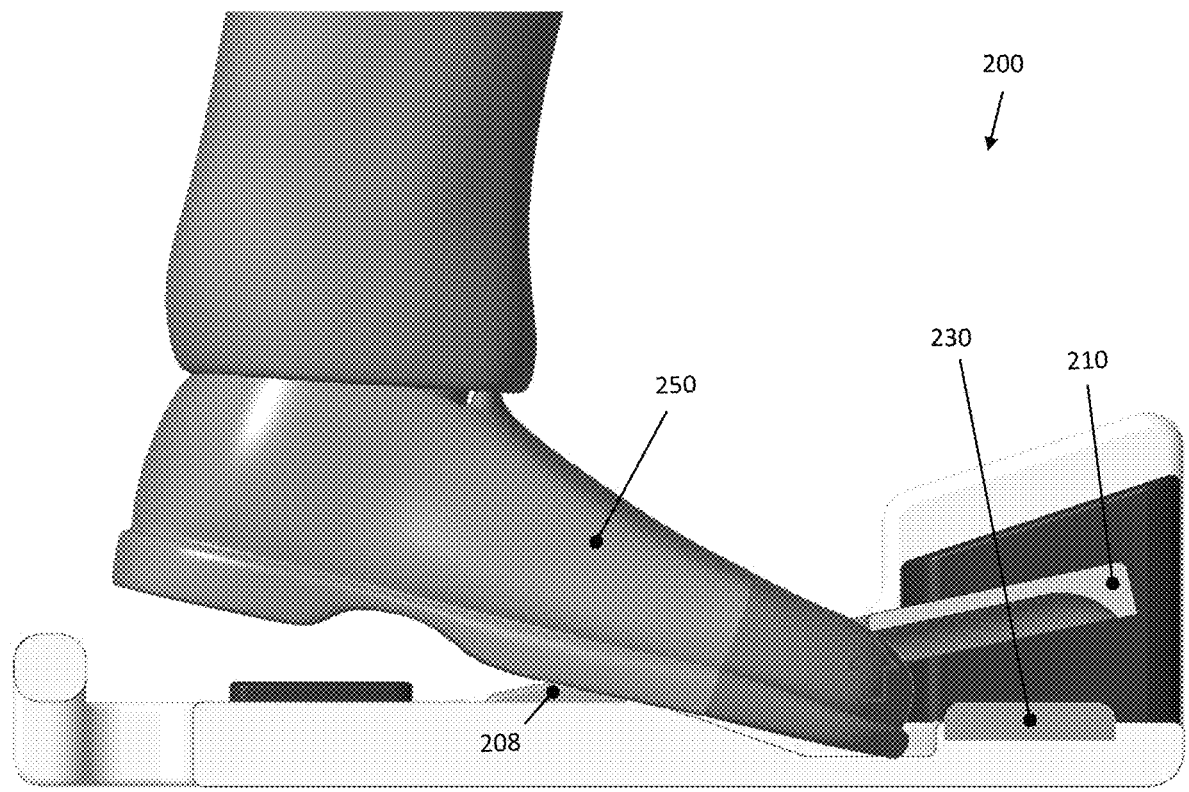
FIG. 5A illustrates a side, cutaway view of a foot controller with the toes of the operator's foot providing an upwards rotational lift on the pedal surface of a treadle.
Figure 5B:
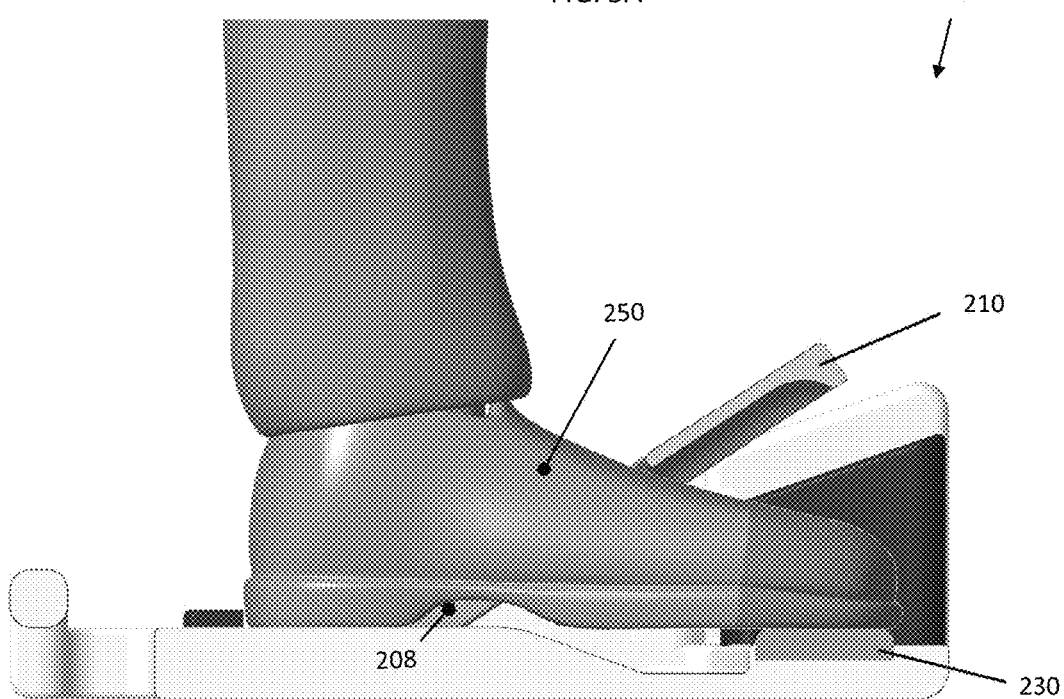
FIG. 5B illustrates the treadle in a lifted position that allows an operator's foot to selectively articulate a switch.

FIGS. 5A-5B illustrate side, cutaway views of the foot controller 200. In FIG. 5A, the toes of the operator's foot 250 can provide an upwards rotational lift (indicated by arrow) on the pedal surface 210 of the treadle 208, thereby exposing the switch 230. FIG. 5B illustrates the treadle 208 in a lifted position allowing the operator's foot 250 to selectively articulate the switch 230. In some cases, the raised rotational position of the treadle 208 after the upward rotational lift of the pedal surface 210 can be maintained (e.g. by one or more ball plunger in the coupling mechanism of the side supports of the treadle 208) until the operator removes his foot from beneath the pedal surface 210 and depresses the pedal surface 210 (e.g. to disengage the ball plungers).

Figure 6:
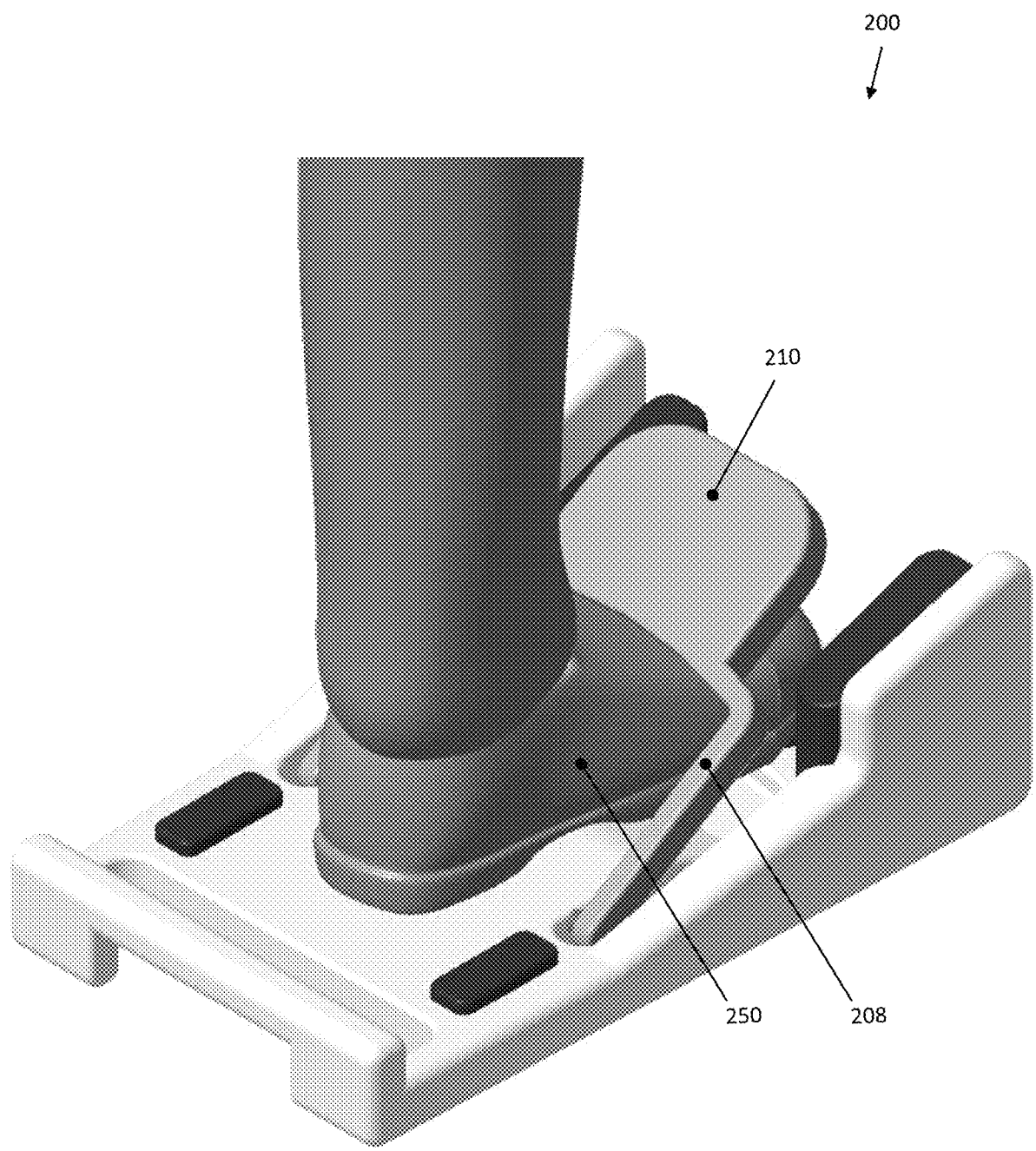
FIG. 6 illustrates a view of a foot controller with the pedal surface of a treadle in a lifted position and with a switch accessed by an operator's foot.

FIG. 6 illustrates another view of the foot controller 200 after the pedal surface 210 of the treadle 208 is lifted and the switch (not shown) is accessed by the operator's foot 250.

Figure 7A:
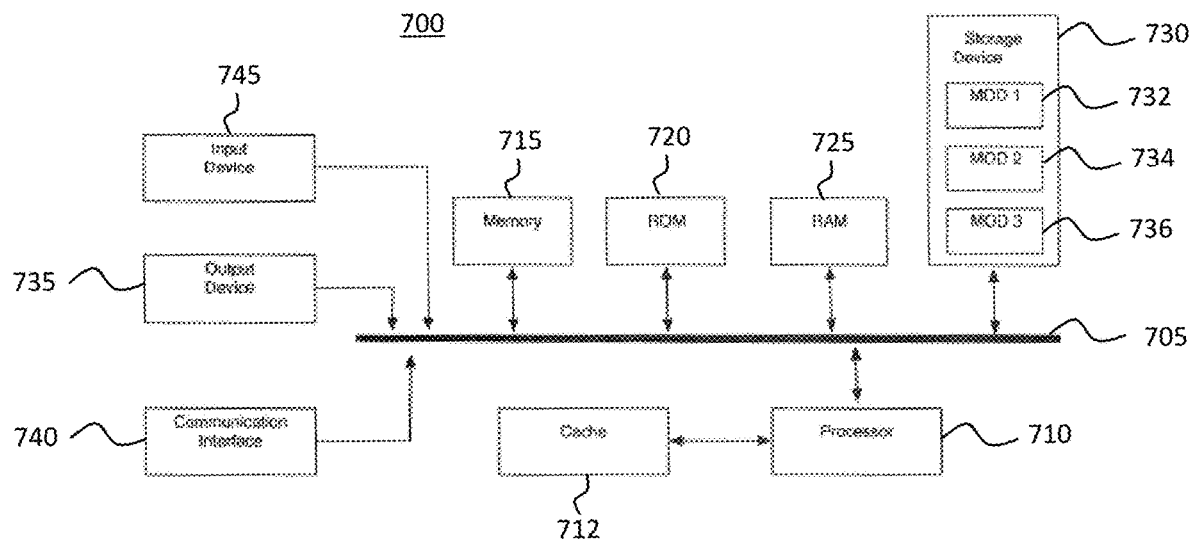
FIGS. 7A and 7B illustrate possible system embodiments.

FIG. 7A illustrates a conventional system bus computing system architecture 700 wherein the components of the system are in electrical communication with each other using a bus 705. Exemplary system 700 includes a processing unit (CPU or processor) 710 and a system bus 705 that couples various system components including the system memory 715, such as read only memory (ROM) 720 and random access memory (RAM) 725, to the processor 710. The system 700 can include a cache of high-speed memory connected directly with, in close proximity to, or integrated as part of the processor 710. The system 700 can copy data from the memory 715 and/or the storage device 730 to the cache 712 for quick access by the processor 710. In this way, the cache can provide a performance boost that avoids processor 710 delays while waiting for data. These and other modules can control or be configured to control the processor 710 to perform various actions. Other system memory 715 may be available for use as well. The memory 715 can include multiple different types of memory with different performance characteristics. The processor 710 can include any general purpose processor and a hardware module or software module, such as module 1 732, module 2 734, and module 3 736 stored in storage device 730, configured to control the processor 710 as well as a special-purpose processor where software instructions are incorporated into the actual processor design. The processor 710 may essentially be a completely self-contained computing system, containing multiple cores or processors, a bus, memory controller, cache, etc. A multi-core processor may be symmetric or asymmetric.

To enable user interaction with the computing device 700, an input device 745 can represent any number of input mechanisms, such as a microphone for speech, a touch-sensitive screen for gesture or graphical input, keyboard, mouse, motion input, speech and so forth. An output device 735 can also be one or more of a number of output mechanisms known to those of skill in the art. In some instances, multimodal systems can enable a user to provide multiple types of input to communicate with the computing device 700. The communications interface 740 can generally govern and manage the user input and system output. There is no restriction on operating on any particular hardware arrangement and therefore the basic features here may easily be substituted for improved hardware or firmware arrangements as they are developed.

Storage device 730 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 725, read only memory (ROM) 720, and hybrids thereof.

The storage device 730 can include software modules 732, 734, 736 for controlling the processor 710. Other hardware or software modules are contemplated. The storage device 730 can be connected to the system bus 705. In one aspect, a hardware module that performs a particular function can include the software component stored in a computer-readable medium in connection with the necessary hardware components, such as the processor 710, bus 705, display 735, and so forth, to carry out the function.

Figure 7B:
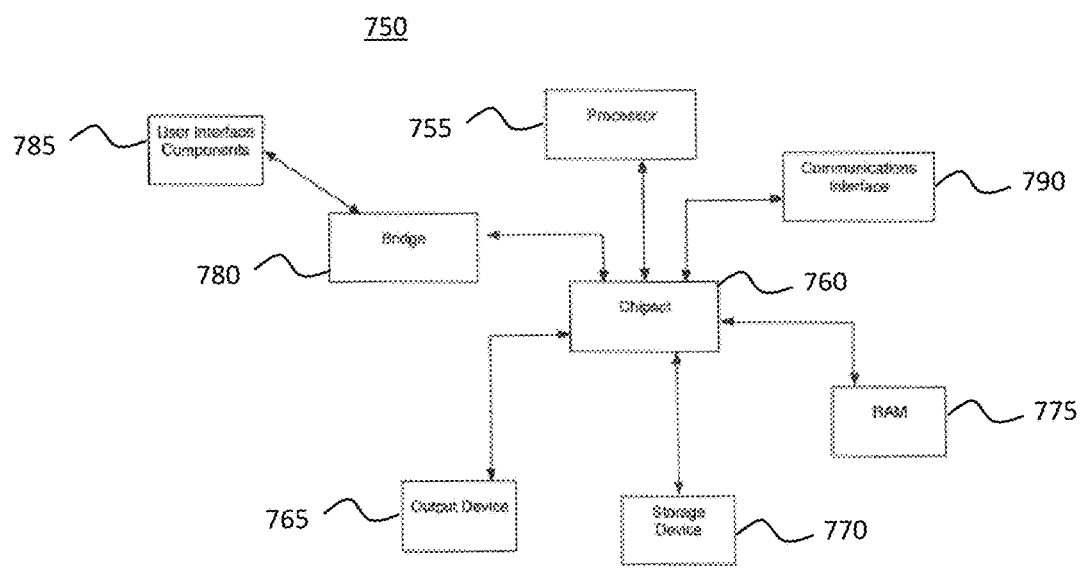

FIG. 7B illustrates a computer system 750 having a chipset architecture that can be used in executing the described method and generating and displaying a graphical user interface (GUI). Computer system 750 is an example of computer hardware, software, and firmware that can be used to implement the disclosed technology. System 750 can include a processor 755, representative of any number of physically and/or logically distinct resources capable of executing software, firmware, and hardware configured to perform identified computations. Processor 755 can communicate with a chipset 760 that can control input to and output from processor 755. In this example, chipset 760 outputs information to output 765, such as a display, and can read and write information to storage device 770, which can include magnetic media, and solid state media, for example. Chipset 760 can also read data from and write data to RAM 775. A bridge 780 for interfacing with a variety of user interface components 785 can be provided for interfacing with chipset 760. Such user interface components 785 can include a keyboard, a microphone, touch detection and processing circuitry, a pointing device, such as a mouse, and so on. In general, inputs to system 750 can come from any of a variety of sources, machine generated and/or human generated.

Chipset 760 can also interface with one or more communication interfaces 790 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 755 analyzing data stored in storage 770 or 775. Further, the machine can receive inputs from a user via user interface components 785 and execute appropriate functions, such as browsing functions by interpreting these inputs using processor 755.

It can be appreciated that exemplary systems 700 and 750 can have more than one processor 710 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A foot controller comprising:
   a base;
   a treadle having a pair of side supports rotatably coupled with the base, the pair of side supports separated by a gap, the treadle further having a pedal surface coupled with the pair of side supports at a distal end of the treadle, wherein the gap between the pair of side supports accommodates an object for providing an upward rotational lift on a bottom surface of the pedal surface;
   a control assembly configured to determine an angular position of the treadle relative to the base and to convert the angular position into a first signal describing an angular position of the pedal surface; and
   a switch configured to emit an additional signal upon depression of the switch, wherein the switch is positioned at a distal end of the base, wherein the switch is at least partially shrouded by the pedal surface at a default angular position of the pedal surface relative to the base, and wherein the switch is at least partially exposed upon an upward rotational lift of the pedal surface away from the distal end of the base;

wherein the switch and the pedal surface are arranged such that the switch is not actuated upon a maximum downward rotational depression of the pedal surface toward the distal end of the base.

2. The foot controller of claim 1, wherein an underside of the pedal surface contains a recess positioned such that the switch is at least partially housed in the recess after a downward rotational depression of the pedal surface toward the distal end of the base.

3. The foot controller of claim 1, further comprising a spring assembly coupled to the base and to the treadle, the spring assembly configured to place the pedal surface of the treadle at the default angular position with respect to the base and configured to compress with an application of torque on the pedal surface by a downward rotational depression of the treadle.

4. The foot controller of claim 1, wherein the foot controller is communicatively coupled with a surgical console, and wherein the first signal describing the angular position of the pedal surface is used to control a surgical tool coupled with the surgical console.

5. A foot controller comprising:
a base;
a treadle having a pair of side supports rotatably coupled with the base, the pair of side supports separated by a gap, the treadle further having a pedal surface coupled with the pair of side supports at a distal end of the treadle, wherein the gap between the pair of side supports accommodates an object for providing an upward rotational lift on a bottom surface of the pedal surface;
a control assembly configured to determine an angular position of the treadle relative to the base and to convert the angular position into a first signal describing an angular position of the pedal surface; and
a switch configured to emit an additional signal upon depression of the switch, wherein the switch is positioned at a distal end of the base, wherein the switch is at least partially shrouded by the pedal surface at a default angular position of the pedal surface relative to the base, and wherein the switch is at least partially exposed upon an upward rotational lift of the pedal surface away from the distal end of the base;
wherein the foot controller is communicatively coupled with a therapeutic laser module, and wherein the additional signal is used to control the emission of one or more lasers from the therapeutic laser module.

6. The foot controller of claim 1, wherein the base comprises a substantially flat surface substantially sized to accommodate an operator's foot.

7. The foot controller of claim 1, wherein the base includes a heel rest area in an area of a proximal end of the base, and wherein the base includes a depression in a substantially flat surface in a position of an arch of an operator's foot when the operator's foot is placed on the base with a heel proximal to the heel rest area and a toe end substantially on the pedal surface.

8. The foot controller of claim 7, wherein the depression allows the operator to insert a top surface of the operator's foot into the depression and under the pedal surface, provide upward rotational lift on a bottom surface of the pedal surface, and actuate the switch with a bottom surface of the operator's foot.

9. A foot controller comprising:
a base;
a treadle having a pair of side supports rotatably coupled with the base, the pair of side supports separated by a gap, the treadle further having a pedal surface coupled with the pair of side supports at a distal end of the treadle, wherein the gap between the pair of side supports accommodates an object for providing an upward rotational lift on a bottom surface of the pedal surface;
a control assembly configured to determine an angular position of the treadle relative to the base and to convert the angular position into a first signal describing an angular position of the pedal surface; and
a switch configured to emit an additional signal upon depression of the switch, wherein the switch is positioned at a distal end of the base, wherein the switch is at least partially shrouded by the pedal surface at a default angular position of the pedal surface relative to the base, and wherein the switch is at least partially exposed upon an upward rotational lift of the pedal surface away from the distal end of the base;
wherein a bottom surface of the pedal surface is rounded for facilitating a smooth entry of the operator's foot and an easy withdrawal of the operator's foot from under the pedal surface.

10. The foot controller of claim 1, wherein each of the pair of side supports are rotatably coupled with the base via a rotational joint, wherein each of the rotational joints includes a ball plunger that interfaces with a feature in the base at a particular raised rotational position of the treadle, thereby maintaining the particular raised rotational position of the treadle.

11. The foot controller of claim 5, wherein an underside of the pedal surface contains a recess positioned such that the switch is at least partially housed in the recess after a downward rotational depression of the pedal surface toward the distal end of the base.

12. The foot controller of claim 5, further comprising a spring assembly coupled to the base and to the treadle, the spring assembly configured to place the pedal surface of the treadle at the default angular position with respect to the base and configured to compress with an application of torque on the pedal surface by a downward rotational depression of the treadle.

13. The foot controller of claim 5, wherein the foot controller is communicatively coupled with a surgical console, and wherein the first signal describing the angular position of the pedal surface is used to control a surgical tool coupled with the surgical console.

14. The foot controller of claim 5, wherein the base comprises a substantially flat surface substantially sized to accommodate an operator's foot.

15. The foot controller of claim 5, wherein the base includes a heel rest area in an area of a proximal end of the base, and wherein the base includes a depression in a substantially flat surface in a position of an arch of an operator's foot when the operator's foot is placed on the base with a heel proximal to the heel rest area and a toe end substantially on the pedal surface.

16. The foot controller of claim 15, wherein the depression allows the operator to insert a top surface of the operator's foot into the depression and under the pedal surface, provide upward rotational lift on a bottom surface of the pedal surface, and actuate the switch with a bottom surface of the operator's foot.

17. The foot controller of claim 5, wherein each of the pair of side supports are rotatably coupled with the base via a rotational joint, wherein each of the rotational joints includes a ball plunger that interfaces with a feature in the base at a particular raised rotational position of the treadle, thereby maintaining the particular raised rotational position of the treadle.

18. The foot controller of claim 9, wherein an underside of the pedal surface contains a recess positioned such that the switch is at least partially housed in the recess after a downward rotational depression of the pedal surface toward the distal end of the base.

19. The foot controller of claim 9, further comprising a spring assembly coupled to the base and to the treadle, the spring assembly configured to place the pedal surface of the treadle at the default angular position with respect to the base and configured to compress with an application of torque on the pedal surface by a downward rotational depression of the treadle.

20. The foot controller of claim 9,
wherein the base includes a heel rest area in an area of a proximal end of the base, and wherein the base includes a depression in a substantially flat surface in a position of an arch of the operator's foot when the operator's foot is placed on the base with a heel proximal to the heel rest area and a toe end substantially on the pedal surface;
wherein the depression allows the operator to insert a top surface of the operator's foot into the depression and under the pedal surface, provide upward rotational lift on the bottom surface of the pedal surface, and actuate the switch with a bottom surface of the operator's foot.

* * * * *